United States Patent [19]

Edelmann et al.

[11] Patent Number: 4,814,144

[45] Date of Patent: * Mar. 21, 1989

[54] CENTRIFUGAL ANALYZER ROTOR UNIT AND INSERT ELEMENTS

[75] Inventors: Hermann Edelmann, Tutzing-Unterzeismering; Anton Pasch, Tutzing; Sigmar Klose, Berg; Hans-Peter Haar; Karlheinz Mann, both of Weilheim, all of Fed. Rep. of Germany

[73] Assignee: Boehringer Mannheim GmbH, Mannheim, Fed. Rep. of Germany

[*] Notice: The portion of the term of this patent subsequent to Jun. 26, 2001 has been disclaimed.

[21] Appl. No.: 559,521

[22] Filed: Dec. 8, 1983

Related U.S. Application Data

[63] Continuation of Ser. No. 323,343, Nov. 20, 1981, Pat. No. 4,456,581.

[30] Foreign Application Priority Data

Nov. 25, 1980 [DE] Fed. Rep. of Germany ....... 3044372

[51] Int. Cl.[4] ............................................. G01N 21/07
[52] U.S. Cl. ....................................... 422/102; 422/72; 356/246
[58] Field of Search ..................... 422/64, 67, 72, 102, 422/104; 436/47; 356/244, 246

[56] References Cited

U.S. PATENT DOCUMENTS

| 3,532,470 | 10/1970 | Rochte | 422/61 |
|---|---|---|---|
| 3,713,775 | 1/1973 | Schmitz | 422/72 |
| 3,744,975 | 7/1973 | Mailen | 422/72 |
| 3,951,608 | 4/1976 | Trod | 422/64 |
| 4,119,407 | 10/1978 | Goldstein et al. | 422/72 |
| 4,225,558 | 9/1980 | Peterson et al. | 422/72 |
| 4,237,234 | 12/1980 | Meunier | 422/72 |
| 4,279,862 | 7/1981 | Bretaudiere | 422/81 |
| 4,314,970 | 2/1982 | Stein et al | 422/72 |
| 4,387,164 | 6/1983 | Hevey et al. | 422/72 |
| 4,390,499 | 6/1983 | Curtis et al. | 422/72 |
| 4,456,581 | 6/1984 | Edelmann et al. | 422/72 |

*Primary Examiner*—Michael S. Marcus
*Attorney, Agent, or Firm*—Sprung Horn Kramer & Woods

[57] ABSTRACT

A rotor unit for a centrifugal analyzer comprises a rotatably-driven circular rotor base; and a rotor head comprising a plurality of insert elements each having at least one chamber sample for the reception of a sample liquid, at least one measuring chamber radially outwardly from the associated sample chamber for the measurement of characteristic parameters for the detection of components of the sample, at least one liquid channel connecting the sample chamber with the measuring chamber and each insert element is releasably mounted on the rotor base at any one of a plurality of different selectable angular positions wherein the insert element is positionally stable when the rotor base is rotating.

9 Claims, 5 Drawing Sheets

FIG. 5
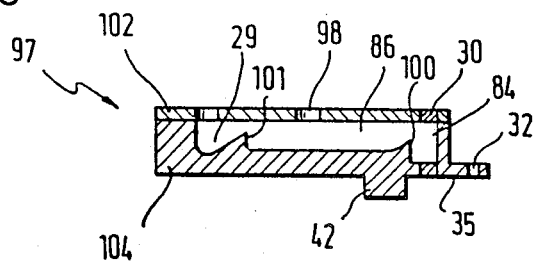
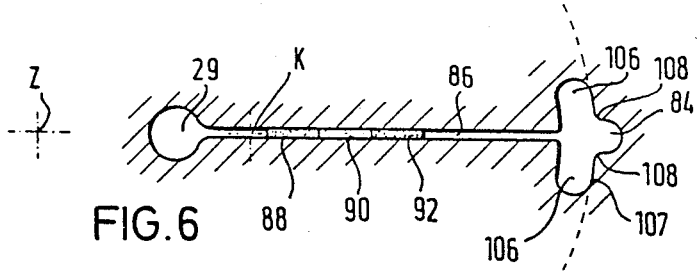
FIG. 6
FIG. 7a
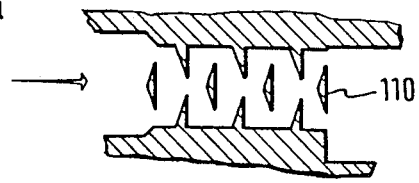
FIG. 7b
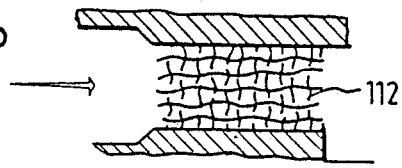

CENTRIFUGAL ANALYZER ROTOR UNIT AND INSERT ELEMENTS

This is a continuation of application Ser. No. 323,343, filed 11/20/81 now U. S. Pat. No. 4,456,581.

BACKGROUND OF THE INVENTION

The present invention is concerned with a rotor unit a centrifugal analyzer with a rotor base connected with a drive a a rotor head which, in operation, is connected with the rotor base. The rotor head includes chambers for the reception of a sample liquid and, radially outwardly from the associated sample chambers, measuring chambers for the measurement of characteristic parameters for the detection of components of the sample, as well as liquid channels for connecting the sample chambers with the measuring chambers. The present invention is also concerned with insert elements and a centrifugal analyzer which are adapted for use with the rotor unit according to the present invention.

Centrifugal analyzers with a rotor unit of the above-mentioned type have been conventional for a number of years for the purposes of chemical analysis, especially in clinical chemistry. They have circularly symmetrically constructed rotor units with a plurality of radial analysis channels. Usually, each analysis channel has, from the inside towards the outside, a trough-shaped reagent space, a sample space and a measuring space which, in the case of the known devices, is constructed as an optcial cuvette. The rotor unit can be arranged in a rotor base and a rotor head mounted non-rotatably on the rotor base. The rotor base is usually constructed as a plate or frame and securely attached to the axis of the rotor drive. The term "rotor head" designates the remaining part of the rotor unit which, in particular, includes the above-mentioned analysis channels. In the case of more recent centrifugal analyzers, the rotor head is, as a unit, exchangeable and is, in operation, non-rotatably connected with the rotor base. The rotor head and the rotor base can, in each case, be constructed in a large variety of ways and can also differ substantially, especially in the diameter of their outer boundary. Thus, the rotor base can, for example, consist of only a holder for the rotor head connected in one piece with the rotor drive axis, which holder is, in operation, completely superimposed by the rotor head.

In the case of the known devices, the rotor head is, while stationary, filled with reagents and samples. A device which can be used for this purpose is described in Federal Republic of Germany Patent Specification No. 2,626,810, which also describes the construction of a typical rotor. As is to be seen from this German Patent Specification, a complicated mechanical device is needed for automatically filling the rotor.

After filling, the known rotor heads are placed in the centrifugal analyzer and connected with the rotor base. The rotor is set in rapid rotation and, in the cae of some devices of this kind, alternating speeds of rotation are used for mixing. Due to the centrifugal acceleration during rotation of the rotor, the reagent passes from its chamber into the sample chamber and then the two together are passed into the measuring chamber, measurement there being carried out with the rotor running. In the case of the known devices, the measurement consists of a determination of the optical density of the liquid in the measuring chambers, which are constructed as optical cuvettes. Thanks to modern electronic evaluation devices, the absorption can be measured in each cuvette at each rotation of the rotor. In this way, the absorption in all cuvettes can be observed almost continuously. In the case of a typical rotational speed of 1000 rotations per minute, 1000 measurements are carried out per minute for each cuvette. On the basis of this process, there is obtained a precision of measurement which, in the case of comparable analysis frequency, can scarcely be achieved with conventional analysis devices, especially in the case of so-called kinetic analysis determinations in which the speed of the course of the reaction permits conclusions to be made regarding the concentration of a particular component.

The known centrifugal analyzers have a number of important advantages but also considerable disadvantages. A summary of the most important requirements for an optimum analysis device can be found in one of the first publications concerning centrifugal analyzers (see Norman G. Anderson in "Analytical Biochemistry", 28, 545–562/1969). One of these requirements is the practically simultaneous measurement of several reactions which, as described above, make possible a better monitoring of the individual courses of reaction. Another requirement is that the volumes of the reagents and samples should be as small as possible. This requirement is also substantially fulfilled by the known centrifugal analyzers but an improvement is still desirable. Centrifugal analyzers readily permit the attachment of modern data evaluation systems for the evaluation of the measurement results, i.e. not only for the conversion of the absorption values into the desired concentration values but also the statistical evaluation of these concentrations in order to give the physician information which is prepared as far as possible.

Other requirements already mentioned in this early article by Anderson are not fulfilled to a desirable extent by the centrifugal analyzers which are at the moment conventional. The known devices still require a large amount of attention from personnel, they are not sufficiently simple to enable them also to be used by untrained personnel and they are not yet sufficiently flexible and variable in order to be able to fulfill very different requirements, especially in the operation of a clinical laboratory.

These deficiencies have, in the course of time, given rise to a large number of developments of the original concept, which have led to increasingly complicated rotor constructions. Thus, these rotors were expensive to produce but are still not able to fulfill all the various requirements of the different analytical determinations which are usual in clinical chemistry.

In particular, the known rotors can only be used for carrying out one analytical determination for a number of samples in one run of the rotor. As a rule, however, in the clinical laboratory a series of different analytical determinations must be carried out on a sample, for example blood from a patient, which, in toto, are also called the profile. In the case of the known analyzers, this necessitates a considerable amount of organization. Thus, the individually necessary analytical determinations, communicated, for example, by the physician to the clinical laboratory, must be carried out gradually in separate rotor runnings on one or more centrifugal analyzers. Thereafter, the separately determined data must be collated and passed on to the physician. This complicated procedure not only requires a considerable amount of organization but is, unfortunately, not infrequently the cause of errors of communication which can possibly result in false therapeutic measures being carried out by the physician. Thus, there is a need for centrifugal analyzers which can be adapted more variably and flexibly to various tasks and which, in particular, can be used for profile analyses or at least for several different analytical determinations in one rotor running. This is especially necessary for emergency analyses where, under certain circumstances, several different analytical determinations must be carried out in the shortest possible time for one sample, i.e. for one patient.

Another problem of clinical chemistry which is not only typical for centrifugal analyzers is that, in the case of the known devices, obtaining the sample, i.e. especially obtaining serum of plasma from blood, and preparing the sample, i.e. especially diluting serum or plasma to the concentrations necessary for the analysis, take place in separate working steps away from the analysis device. It is readily apparent that, in this way, additional manual working steps and, in particular, decanting steps are necessary. These can, in turn, again result in mistakes being made or can, for example, also result in contamination of the samples.

SUMMARY OF THE INVENTION

It is an object of the present invention to construct a rotor unit for a centrifugal analyzer of the initially described type so that, with avoidance of the disadvantages of known centrifugal analyzers, the simplest possible operation is possible, together with the most flexible and wide use is possible of the device. Furthermore, the object of the present invention is to provide insert elements for use in a rotor unit according to the present invention, as well as an appropriately constructed centrifugal analyzer.

Thus, according to the present invention, there is provided a rotor unit for a centrifugal analyzer with a rotor base connected with a drive and a rotor head which, in operation, is connected with the rotor base, said rotor head including chambers for the reception of a sample liquid and, radially outwardly from the associated sample chambers, measuring chambers for the measurement of characteristic parameters for the detection of components of the sample, as well as liquid channels for connecting the sample chambers with the measuring chambers, wherein the rotor head comprises a plurality of different insert elements which are exchangeable and connectable with the rotor base at different selectable positions, said insert elements being positionally stable when the centrifugal analyzer is in operation.

Each insert element contains devices for carrying out part stages of analytical determinations. The external shape of the insert elements can differ but they can, for example, also only differ in the chemical composition of a part of their components. It is important that, by means of the present invention, instead of the previously conventional, uniformly constructed rotors, those are used, the rotor head of which can receive a plurality of different insert elements, a substantially increased variability thereby being achieved. Whereas the known rotors, as mentioned above, were only capable of fulfilling one particular task, namely, as a rule, the determination of one chemical components of a sample on a plurality of samples in one rotor running (so-called "batch" operation), in the case of the rotor unit according to the present invention, each insert element can be optimally adapted for a particular task. Due to the possibility of connecting a plurality of different insert elements with the rotor base, for each rotor running an individually adapted rotor can be assembled which can be then used in a substantially more varied manner. For example, in this manner, determinations of several components of a sample (profile determination) are possible in one rotor running. Furthermore, there are considerable handling simplifications, such as are described hereinafter.

According to a preferred embodiment of the present invention, the insert elements used can be analysis elements of various constructions, such as simple analysis elements which include devices for determining one of the components of a sample and also multiple analysis elements which have devices for simultaneously determining several components of one or more samples. These insert elements can now be adapted entirely to a particular analytical task. Thus, in their construction, they can have different analysis channels which are supplied with liquid reagents. However, they can also contain pre-packed reagents, especially in solid form, which then, as will be described hereinafter, are dissolved by the diluted sample and mixed therewith. The term "insert element" or "analysis element" includes those of every possible shape and size. Especially simple analysis elements can be, for example, papers or fleeces impregnated with reagents which can be exchangeably inserted into the rotor head.

According to another preferred embodiment, the insert elements according to the present invention connectable with the rotor base include elements for obtaining and preparing the samples. In this way, a substantial disadvantage of the known centrifugal analyzers is also overcome. Thus, hitherto the sample was, in each case, obtained and prepared separately from the analysis device. In the case of blood analysis, the blood must first, for example, be centrifuged for obtaining serum or plasma and this then appropriately diluted before it can be introduced into the sample chambers of a centrifugal analyzer. For transferring the samples into the rotor head outside of the apparatus, use was made, as mentioned hereinbefore, of complicated apparatus or manual pipetting was necessary. With the insert elements according to the present invention, hereafter described in more detail, for obtaining and/or preparing the sample, it is now possible to carry out these important steps in the centrifugal analysis device without manual transfer procedures or other manual handling steps being necessary. In this way, not only is the operating simplified but the prevention of human errors also increased the dependability.

The spatial measurements of the insert elements are preferably supplemented in such a manner that larger elements can be connected to the rotor base in place of an integer multiple of the smallest elements. This embodiment of the present invention can also be expressed in such a manner that the dimensions of the insert elements contain a raster measure. A particular whole number fraction of the rotor surface or of the rotor circumference determines the base unit of the raster. The individual insert elements are then so constructed that their spatial requirement corresponds to a multiple of this raster base unit. In this manner, the rotor unit according to the present invention becomes especially variable because comparatively large insert elements can now without waste of space, occupy the place of several smaller insert elements. The holders of the insert elements are, for the same reason, preferably arranged periodically on the rotor base, insofar as they each lie on the same circumference, the periodicity length of the holder arrangement thereby corresponding to the base unit of raster.

It is to be expressly pointed out that the present invention is not limited to the case in which the insert elements all have about the same radial distance from the center of the rotor. On the contrary, for certain uses it can be highly desirable to arrange the insert elements on different circumferences of the rotor, for example in order thus to permit different centrifugal accelerations to act upon the different elements at a particular speed of rotation. In this case, the holders for the insert elements also have a different radial distance from the rotor center and thus lie on different circumferences.

A construction of the insert elements which, viewed from the top of the rotor, has a circular sector shape is especially preferred because various insert elements thereby jointlessly abut one another and, from the totality of the insert elements, there is obtained an uninterrupted surface of the rotor head when the rotor is completely loaded with insert elements, although this is not essential. The term "circular sector shape" is to be understood here to mean that the bounding lines of the sectors, i.e. viewed from the top of the rotor, extend essentially along the radii of the rotor circle. Of course, the present invention also includes solutions to the problem in which the outer edges differ from the course of these radii in a definite manner which repeats itself in the case of the different elements so that the different insert elements, although they do not have straight side surfaces, as a whole give an uninterrupted loading of the rotor base. Such a construction can be especially advantageous in order to hold together the insert elements by a form-locking construction of their side surfaces.

In conventional centrifugal analysis rotors, it is known to construct the rotor head in two parts, i.e. in a ring on the periphery of the rotor head, which contains cuvettes for optical measurements and an inner part, constructed, when viewed from above, in circular form which fits the cuvette ring exactly and, on its periphery, has through openings which, in the assembled state, are in alignment with and tightly close the entry openings of the cuvettes. Upon rotation of the rotor, the analysis liquid then passes from the analysis channels in the circular inner part into the cuvettes of the cuvette ring. Such a construction has the advantage that the cuvette ring can be made from high quality materials and made very precisely so that the cuvettes have very good optical properties, whereas the circular inner part can be made comparatively simple. Consequently, a preferred embodiment of the present invention is also correspondingly constructed. In this case, the cuvette ring is to be regarded as being a part of the rotor head and is securely or exchangeably connected with the rotor.

All the measuring chambers preferably lie on one circumference of the rotor head, i.e. they have the same radial distance from the center thereof, in order that a single evaluation unit suffices for the determination of the characteristic parameter which must be measured for the detection of components of the sample. As already mentioned, in the case of known centrifugal analyzers and preferably also in the case of the device according to the present invention, the optical absorption at one or more wavelengths is determined as the characteristic parameter for the detection of components of the sample. However, the present invention is not limited to such optical measurements. Precisely because of the novel variability of the device according to the present invention, it is also possible to carry out completely different determinations in a centrifugal analyzer, these including, for example, electrical measurements in conjunction with electrochemical analysis processes of the most varied types. In this case, the measuring chambers have electrodes, the signals of which are passed in an appropriate manner to the evaluation apparatus of the device, for example via sliding contacts or without the use of wires. In such cases, but also in the case of purely optical measurements, the measuring chambers can also lie on different circumferences of the rotor head.

The sample obtaining and/or sample preparing elements have take-off points at which, by means of appropriate devices of the apparatus, for example canulae of automatic measuring devices or so-called dispensers or dilutors, samples can be taken. These take-off points preferably lie on an arc with the same radius as the feed-in openings of the sample chambers of the analysis element. It is thereby possible, for the transfer of the samples from the sample obtaining or sample preparing elements to the analysis elements, to use measuring devices which only move in a vertical direction. The rotor is then brought into a position appropriate for the removal or supply procedure by means of a step-by-step switch device integrated into the drive.

According to a further preferred embodiment, the insert elements carry codings with regard to the sample and/or the components of the sample to be determined with the particular element. These codings can be read by a reading means incorporated into the centrifugal analyzer in order, in this way, to impart to the device essential data for the evaluation and, at the same time, to obtain a control for the correct supplying of the rotor with the insert elements by the operating personnel. Furthermore, the insert elements preferably have markings for triggering the measurement procedure. The insert elements have, of course, in their position with regard to the rotor base, certain tolerances, even though these may be small in the case of prevision construction of the holder. Since, in general, the measurement procedure must be triggered with regard to the position of the insert element, it is especialy advantageous when the markings in question are on the insert element and not, for example, on the rotor base.

The holding parts which, by form-locking cooperation with the insert elements are preferably used for their precise holding on the rotor base, are preferably arranged in the region of the measuring cells. Possible tolerances in the dimensions of the insert elements thereby have especially little effect with regard to the positioning of the measuring cells.

The present invention also provides insert elements for use with the rotor unit according to the present invention, which insert elements are especially adapted for this purpose and make possible further preferred embodiments of the rotor unit according to the present invention.

Preferred insert elements of this kind include the reagents for carrying out analytical determinations in a form which is storage-stable and which can be transported with the insert elements. Such analysis insert element are especially advantageous for use as "once only" elements, which can also be called disposable elements. They are already provided by the manufacturer with appropriate reagents for particular analyses and are supplied to the user as a unit containing the reagents. This obviates the handling of individual and especially of liquid reagents, which is a considerable simplification. Such disposable elements can be made in a large number of versions, each version being suitable for one or more identical or different analysis methods and includes the appropriate reagents, as well as appropriate shaped fluid channels and other devices. For carrying out a plurality of different analytical determinations, the user has then only to select the appropriate insert element and to place it into the rotor unit according to the present invention.

An especially preferred insert element for use in the rotor unit according to the present invention contains at least one analysis reagent in dry form and a plurality of very small hollow spaces connected with one another, which connect the sample chamber and measuring chamber with one another. Such insert elements are described in our simultaneously filed Federal Republic of Germany Patent Application No. 30 44 385. Reference is made to the whole content of this Patent Application. Details of the construction of the insert elements described therein, which are also important components of the present invention and permit an especially advantageous use thereof, are described in detail in this co-pending German Patent Application, reference to which is hereby made without repeating the content of this German Patent Application.

Other preferred insert elements, namely sample obtaining and/or preparing elements, can be used for taking blood from a patient, for obtaining serum or plasma by the action of centrifugal acceleration and as sample vessels. These elements intended for blood analysis have two additional vessels, namely, a syringe for taking blood from a blood vessel of a patient and a centrifuge tube for obtaining serum or plasma. At the same time, transfer procedures from one vessel to another are avoided. However, in conjunction with the present invention, it is especially important that the obtaining and preparation of the sample, as already mentioned hereinbefore, can, in the case of using such insert elements, take place in the analysis apparatus itself and that the sample is then, without manual steps, transferred in a simple way from the sample obtaining and/or preparing vessel in the analysis apparatus itself into the analysis element.

For a thermostatic control of the sample, it is also advantageous when these sample obtaining and/or preparing elements are used in the rotor unit itself according to the present invention. Thermostatic control can be ensured by an appropriately regulated heating of the rotor base and/or of a part of the rotor head which is not exchangeable with the insert elements, be it by a thermostated fluid flow or by direct electrical heating or cooling. In order to achieve a sufficiently precise thermostatic control of the sample, this must be in thermal contact with the thermostatically controlled parts for a certain minimum period of time. If the obtaining and preparation of the sample take place away from the rotor, then, after introducing the sample into the rotor head connected to the rotor base, it is necessary to wait until the time has expired which is necessary for this thermostating. In contradistinction thereto, the sample in the device according to the present invention is already thermostated during the centrifuging and possible further process steps, for example during dilution of the sample. Therefore, the analytical procedure can commence shortly after transferring the sample into the analysis insert element. The saving of time thereby resulting results in a greater analysis capacity of the apparatus or in an increased exactitude due to the improved thermostating.

The rotor unit according to the present invention is preferably employed in a specially construction centrifugal analyzer which, in particular, includes evaluation devices for the determination of several different components of a sample in one rotor running. As mentioned thereinbefore, the present invention makes possible, in a simple manner, the determination of several different components of a physiological liquid in one rotor running. The determination consists of a chemical reaction and the subsequent measurement of a parameter, the value of which is characteristic for the concentration of the component to be determined. There is a number of known and proven specific chemical reactions for various components of a sample, especially in clinical chemistry, which result in a change of the same parameter characteristic for the concentration, for example the optical absorption of the solution at a particular wavelength. By way of example, mention is made to the numerous reactions which result in a change of the concentration relationship of NAD and NADH, the absorption of the solution at 340 nm being characteristically influenced. Such determinations, which result in a change of only one characteristic parameter, can be evaluated with conventional centrifugal analyzers. However, in order to fully utilize the versatility of the novel analysis device according to the present invention, it is advantageous when the centrifugal analyzer employed can evaluate several parameters in one rotor running. In principle, these can also be of a different nature, for example, the measurement of the optical absorption and of the fluorescence and, under certain circumstances, of electrical values. However, a centrifugal analyzer is especially preferred which can be used for determination of the optical absorption at several different wavelengths in one rotor running, for which purpose it has a polychromic photometer. The term "polychromic" here is not to be understood to mean that the photometer operates with multicolored light but that it must be a photometer which can measure at a number of different wavelengths, the change of the wavelength being so coordinated with the course of the measuring cuvettes of the rotor that the absorption of each cuvette can be measured at any desired wavelength.

Furthermore, a centrifugal analyzer adapted for use with the present invention preferably also has a rotor drive which not only, as in the case of the known apparatus, is suitable for driving the rotor at a speed of rotation appropriate for the mixing and measuring procedures (usually about 1000 r.p.m.) but, in addition, has a higher speed of rotation for centrifuging samples. Furthermore, the drive is preferably to be capable of moving the rotor stepwise into certain positions, which is of especial advantage for the preparation and distribution of the samples.

The present invention will now be described in more detail, with reference to the accompanying drawings, which illustrate several specific embodiments and in which:

BRIEF DESCRIPTION OF THE DRAWINGS

FIG. 5 is a cross-section through an analysis insert element for use with liquid reagents;

FIG. 6 is a schematic illustration of a top view of a preferred construction of an analysis channel; and FIG. 7a and 7b are cross-sectional views through a part of an analysis channel present in an analysis element according to the present invention, with additional mixing devices.

DETAILED DESCRIPTION OF THE INVENTION

Figure 1:
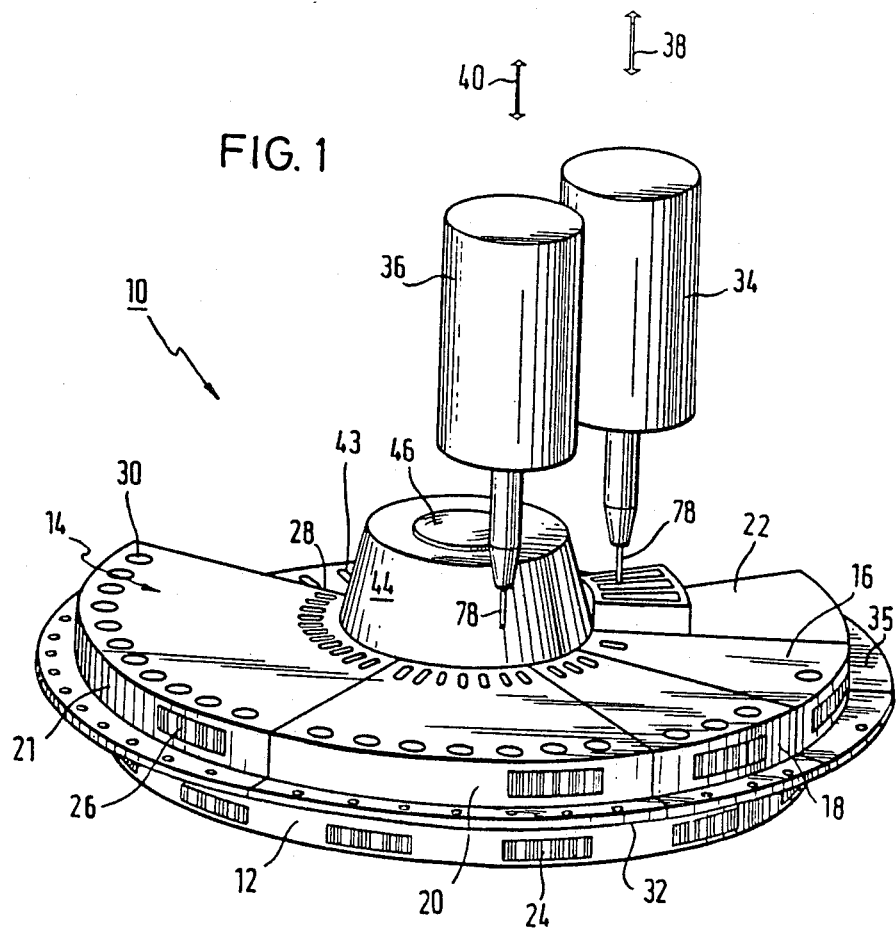
FIG. 1 is a perspective schematic illustration of a rotor unit according to the present invention.
Figure 2:
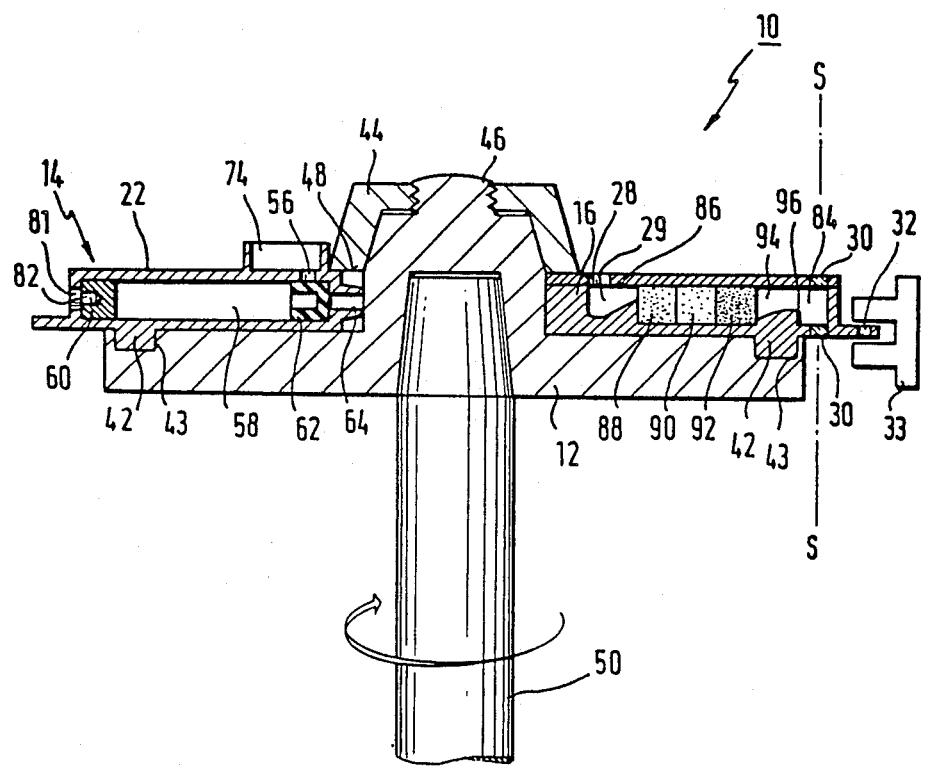
FIG. 2 is a cross-section through a rotor unit according to FIG. 1.

FIGS. 1 and 2 illustrate a rotor unit, indicated as a whole by 10, with a rotor base 12 and a rotor head 14. The term "rotor head" includes all the constructional parts which can be connected with the rotor base for the operation of the centrifugal analyzer. In particular, it includes the constructional elements necessary for the actual analysis. Those include, according to the present invention, in the first place various analysis insert elements, for example simple analysis elements 16 and multiple analysis elements, such as the illustrated triple analysis element 18, the sevenfold analysis element 20 and the elevenfold analysis element 21.

Furthermore, a combined sample obtaining and preparing element is indicated by 22. Not only on the rotor base 12 but also on the insert elements 16, 18, 20, 21 and 22, there are provided mechanically readable codings 24 and 26, respectively. The analysis elements have inlet openings 28 for the introduction of a sample into the sample chambers 29, cuvette windows 30 and bores 32 which serve as trigger marks for the initiation of the measuring procedure. In FIG. 2 there is schematically illustrated a trigger signal emitter 33 which contains a source of light and an optical receiver in order to produce a trigger signal each time upon passing a trigger bore. The path of light for the optical absorption measurement passes along the line S—S in FIG. 2 but, for the purpose of clarity, it is not shown in detail. It is of conventional construction, a polychromic photometer preferably being used.

In the case of the embodiment of the present invention illustrated in the FIGURES, an optical absorption measurement is employed as the characteristic parameter for the detection of components in a sample. This is the most conventional analysis process in clinical chemistry but the present invention can also be applied to other analytical principles in which, as the characteristic parameter, for example the fluorescence, the luminescence, the reflection, the radioactivity or electrical data of the reagent mixture are measured in the measuring chamber in order to determine therefrom the concentration of certain components of a sample, for example of enzymes of substrates in a physiological liquid.

In FIG. 1, there can be seen two measuring devices 34 and 36 which serve for measuring, diluting and distributing the samples. There is preferably used a sample-reagent measurer 34 which, in general, can also be called a diluter, and a sample distributor 36 which, in general, can be called a dispenser. Both of them are arranged to be movable vertically in the centrifugal analyzer according to the present invention, as is indicated by the double arrows 38 and 40.

The insert elements 16, 18, 20, 21 and 22 can be connected by holding pins 42 to the rotor base 12, which has corresponding holding slots 43 (see FIG. 2). The shapes of the holding slots 43 and of the holding pins 42 are so adapted with regard to one another that they fit into one another and ensure a position-stable arrangement of the insert elements 16, 18, 20 21 and 22. For fixing the insert elements, there is also provided a central locking member 44 which, by means of a thread 46, can be screwed on to the rotor base 12 and which lies upon seatings 48 of the insert elements 16, 18, 20, 21 and 22. The rotor base 12 is connected via a driving axis 50 to a rotor drive for the centrifugal analyzer. The quality of the mounting of the driving axis and the weight of the rotor base are important for a low vibration running of the rotor. Furthermore, the weight distribution of the insert elements is preferably such that, even in the case of different loading of the rotor, not too great an imbalance results. Insofar as the rotor is not completely loaded, it can be necessary to apply appropriate weights to the rotor base in order to avoid too great an imbalance.

Figure 3:
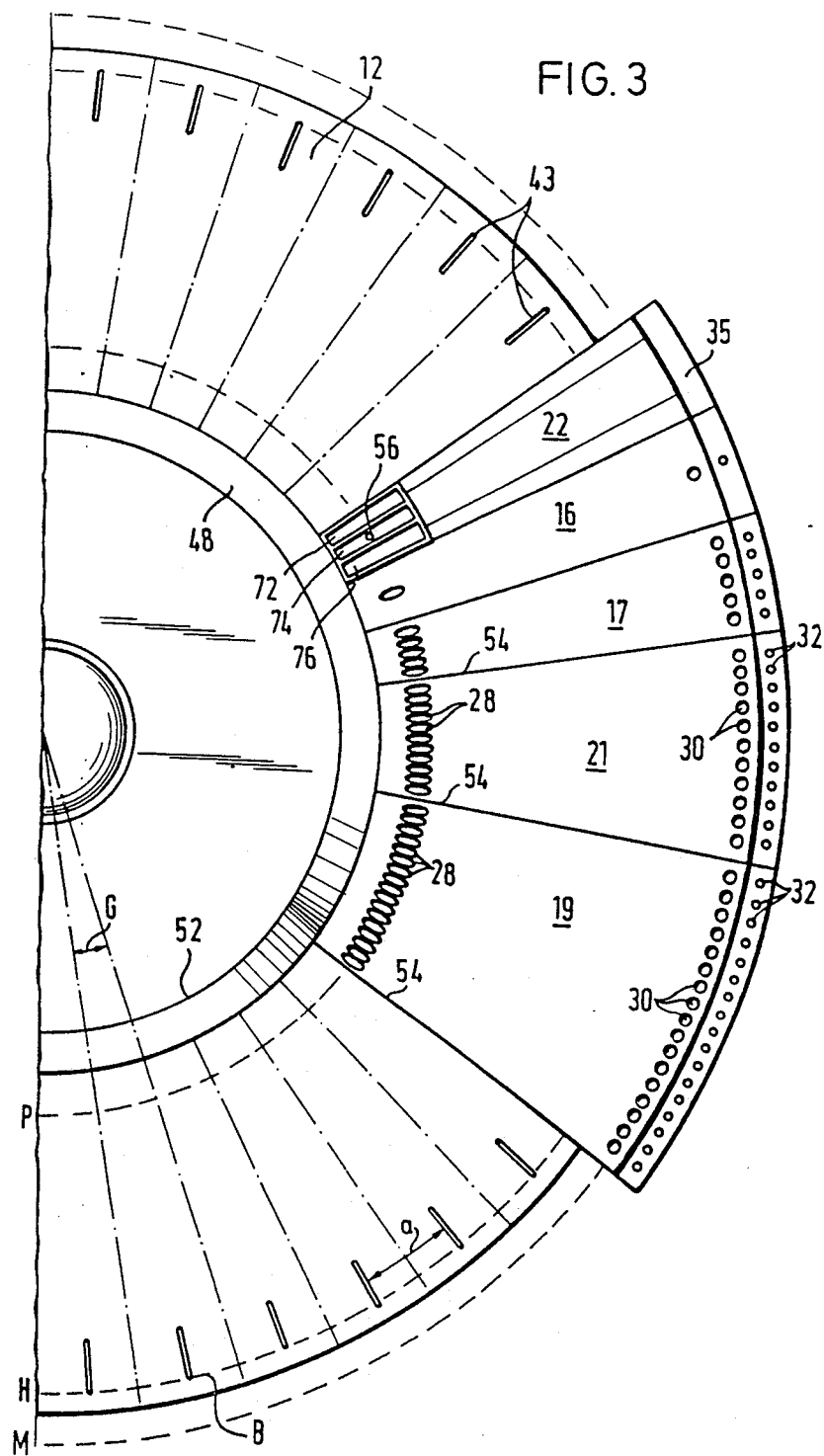
FIG. 3 is a top view of a rotor unit according to the present invention from which, in particular, the raster division can be seen.

FIG. 3 shows a top view of a centrifugal analyzer according to the present invention which differs from that illustrated in FIGS. 1 and 2 in that it has places for a larger number of insert elements. FIG. 3 clearly shows, in particular, the advantageous rastering according to the present invention of the fixing means and thus of the arrangement of the insert elements 16, 17, 19, 21 and 22, which can be changed as desired. It can be seen that the circular surface of the rotor base 12 is divided up into a plurality of whole segments B of the same size. In the illustrated embodiment, these segments are sectors of a circle which are cut off on a radius corresponding to the inner boundary 52 of the seating 48. Each sector corresponds to a definite angular measurement of the circle which is characterized as the basic unit of the raster of the insert element arrangement and is indicated in the FIGURE by reference G.

As can be seen from FIG. 3, in the case of a preferred embodiment, all the holding slots 43 for the insert elements are arranged on the same circumference H. The arrangement is periodic with the periodicity length a. It is important for the present invention that the periodically length a corresponds to the basic unit G of the raster. It is thereby possible to combine with this insert elements of different sizes, for example elements 17, 19 and 21, as desired and without waste of space on the various places of the rotor base.

In contradistinction to FIG. 1, FIG. 3 shows analysis elements with five, eleven and seventeen analysis channels, indicated by 17, 21 and 19, respectively. The illustrated elevenfold analysis element 21 corresponds in size to two base units of the raster G and has two holding pins 42 on its under side. The seventeenfold analysis element 19 has a size corresponding to three raster base units G and three holding pins 42. It can easily be seen that, due to this construction according to the present invention, an especially advantageous arangement of various insert element on the rotor base is possible.

The illustrated embodiment is especially simple in that the insert elements have, per raster unit of their size, only one holder and are constructed as simple sectors with straight side edges. However, the present invention includes a number of more complicated constructions of the insert elements. Thus, several holders per raster base unit bring about an improved positioning of the elements. A construction of the side edges 54 deviating from a straight line can also improve the engagement from element to element and thus the exactitude of the arrangement thereof on the rotor base 12. Insert elements which do not touch one another and are fixed spaced apart on the rotor base can be of advantage in certain cases. The insert elements do not all have to be arranged with the same radial distance from the center of the rotor. In this case, not all of the holders are present on the same circumference but, in this case, too, it is advantageous when the periodicity length of the holders present approximately on the same circumference correspond to the base unit of the particular associated insert element raster. In all cases, it is important that the spatial measurements of the insert elements and the arrangement thereof are so adapted with regard to one another that larger elements can be accommodated in place of a number of the smallest elements. The rastering according to the present invention can thereby be used in a number of variations.

As can also be seen from the number of inlet openings 28 and curette windows 30 of the analysis elements in FIG. 3, the multiple analysis elements 17, 19 and 21 each have a number of analysis channels which is a multiple of six less one. In general, it can be said that multiple analysis elements of the type according to the present invention preferably have a number of analysis channels which corresponds to a whole number multiple of a base number less one, the base number being the maximum number of analysis channels of the smallest analysis element plus one. The described preferred number of analysis channels of the multiple analysis elements gives, in the case of the above-described raster division, an optimal utilization of the elements but it should be borne in mind that the side edges of the insert elements have a certain spatial requirement which, in each case, corresponds approximately to the spatial requirement of one analysis channel.

All of the cuvette windows 30 are on a common measurement circle which is shown by a broken line and indicated by M. In this way, a single photometer suffices for all the measurements. According to the present invention, the inlet openings 28 of the sample chambers 29 in the analysis elements are also present on the same circumference as the removal opening 56 of the combined sample obtaining and preparing element 22. This sample circle P is also illustrated by a broken line.

Figure 4:
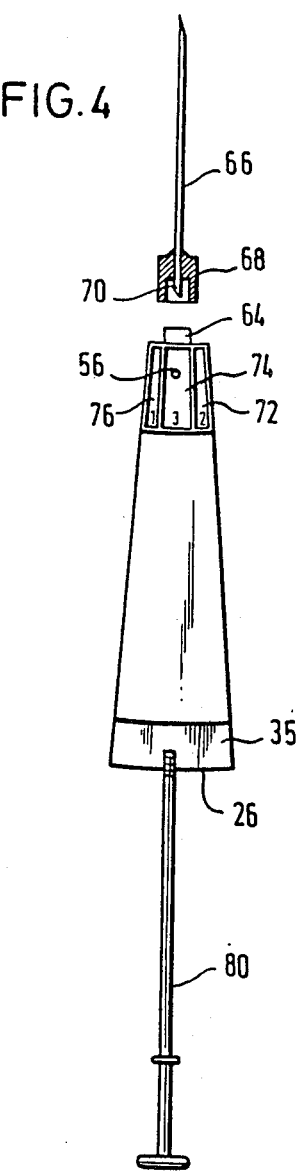
FIG. 4 is a schematic illustration of a view of a combined sample obtaining and preparing element.

On the left side of FIG. 2 there can be seen the combined sample obtaining and preparing element 22 in cross-section. In FIG. 4 it is again illustrated in top view with the associated components. As shown in FIG. 2, it preferably has a cylindrically-shaped inner chamber 58, the circular cross-section of the cylinder lying in a plane at right-angles to the plane of the paper in FIG. 2. On the lower end of the insert element 22 on the left side in FIG. 2, there is a piston 60 in the inner chamber 58. On the end opposite to the piston, the inner chamber 58 is closed by an elastic stopper 62 made of rubber-elastic material which, according to FIG. 2, has a U-shaped cross-section. On the same end, as shown in FIG. 4, there is a connecting part 64 for an injection needle which can be connected with the insert element via a connecting piece 68 cooperating with the connecting part 64. The rear pointed end 70 of the injection needle 66 thereby penetrates into the closure stopper 62 of the insert element shown in FIG. 2, an outwardly sealed off fluid connection thereby being produced between the hollow space of the needle 66 and the inner chamber 58 of the insert element 22.

In the assembled state, there is found upwardly, in the region of the closure stopper 62, the take-off opening 56 of the combined sample obtaining and preparing element 22. It opens in the middle chamber of three dilution chambers 72, 74 and 76 (see FIGS. 3 and 4). Similarly to the connection of the injection needle 66, the take-off opening 56 is penetrated by a needle-like canula 78 of the corresponding diluter 34 and is again closed when the canula 78 of the diluter 34 is pulled out.

On the radial outer end of the insert element 22, there can be connected a piston rod 80 which, passing through bore 81, engages in a recess 82 of the piston 60 and can be positively connected therewith.

The combined sample obtaining and preparing element 22 according to the present invention is used as follows:

First it is provided at the intended places with the injection needle 66 and the piston rod 80 and the piston 60 is brought into the radially inner-lying position (in FIG. 2 towards stopper 62. The needle can then be inserted into the blood vessel of a patient in order, in conventional manner, to remove blood as with a syringe, by pulling back the piston 60. The piston is drawn back completely, the piston rod 80 and the injection needle 66 are removed and the insert element 22 is placed into the analyzer. After the rotor unit 10 according to the present invention has been loaded to the necessary extent for a particular measurement, a centrifuging run is carried out in the manner described hereinafter in more detail. The solid components of the blood thereby collect on the radially outer end of the insert element 22, whereas radially more towards the interior of the inner space 58 it is filled with serum or, if an appropriate coagulation agent has been added, with plasma. The further analysis steps are described in more detail hereinafter in connection with the description of the total function of the apparatus according to the present invention.

Details of the construction of the analysis elements are to be seen, in particular, in FIGS. 2, 5, 6 and 7. In FIG. 2, the analysis channel of an especially preferred analysis element can be seen in cross-section. This is indicated in the FIGURE with 16 as being a single analysis element. However, it is to be stressed that the here-described construction of an analysis channel, as well as a number of other constructions adapted to a particular analytical purpose, can, if desired, also be used in a multiple analysis element, for example the elements 18, 20 and 21. For the variability achieved by the present invention, it is important that various analysis insert elements are constructed in different ways, whereby not only the chemicals provided but also the physical construction of the analysis channels can differ from one element to another and, in the case of multiple analysis element, also within one element, depending upon the purpose of the element, this depending upon the analytical determinations to be carried out with the element.

The analysis element illustrated in cross-section in FIG. 2 has a sample chamber 29, a measuring chamber 84 and a fluid channel 84 joining the two which, in the present case, has, in the plane of the drawing of FIG. 2, a substantially rectangular cross-section and, at right angles to the plane of the drawing, only has a comparatively small lumen. In a practical case, the height of the fluid channel 86 is 6 mm. and the breadth 1 mm. The capacity of the sample space 29 is, in the case of this embodiment, about 20 ul. In the fluid channel 86, there are fleece papers 88, 90 and 92 containing appropriate dry reagents for a particular analysis. They have a plurality of small hollow spaces connected with one another in which are present the reagent and in which, at the same time, a distribution and mixing up of the diluted sample takes in or with the reagents, as is described in our above-mentioned co-pending Federal Republic of Germany Patent Application No. 30 44 385. Radially in an outward direction, the fluid channel has a connecting channel 94 which opens into the measurement chamber 84. Radially inwardly, chamber 84 is bounded by a barrier 96. The measurement chamber 84 is so dimensioned that the simple-reagent mixture fills it, in the case of centrifuging, to such an extent that the cuvette window 30 is completely in the region of the fluid.

In principle, the analysis procedure takes place in such a manner that the sample, i.e. the serum or plasma in the necessary dilution, passes through the opening 28 and into the sample chamber 29. The rotor is then set into motion and the sample fluid penetrates into the fleece papers 88, 90, 92, dissolves the reagents and, together with these, passes into the measurement chamber. There, during the centrifuging, in principle similarly to the case of the known centrifugal analyzers, a determination is carried out of the optical absorption in order to obtain therefrom the desired concentration of a component of the sample. Further details are described in our above-mentioned co-pending German Patent Application and hereinafter in a specific Example.

High requirements are demanded of the material used for making the insert elements and especially for the analysis elements. It must be inert to the physiological fluids and reagents which come into contact with it and yet must be capable of being worked into the necessary shaped in an economic manner. Furthermore, the cuvette windows 30 must be transparent in the necessary spectral range. This is something of a problem, especially in the case of the low wavelengths employed for analytical purposes (for example 340 nm.). Although, in the described embodiment, the cuvette windows 30 are illustrated as elements inserted into an injection molded part, it can be desirable to produce a larger part or even the whole of the upper and lower sides of the analysis element from an appropriate transparent synthetic resin. Between these transparent synthetic resin surface there is then present, in a sandwich-like manner, a middle part which laterally bounds the analysis channel with the sample chamber 29 and the measuring chamber 84. The whole insert element can, of course, also be made of transparent material. Preferred optically transparent materials include, for example, polymethyl methacrylate and polystyrene.

As already mentioned hereinbefore, the trigger bores are preferably provided in the analysis elements 16 to 21 and not, for example, in the rotor base in order to ensure a precise arrangement of their position with regard to the cuvette openings 30. A further advantage of this arrangement is that a measurement procedure is actually only triggered off at rotor positions at which it is also necessary. Thus, for example, the sample obtaining and preparing element 22 has an uninterrupted shutter surface 35 and a single analysis element 16 only one trigger mark whereas the equally large triple analysis element 18 and the fivefold analysis element 17 have three and five marks respectively. If the trigger marks were provided on the rotor base and thus were not exchangeable with the insert elements, the measurement procedures would also be trigger off on those positions at which no measurement is necessary. Especially in the case of the use of a flashlamp for the photometer of the centrifugal analyzer, a considerable saving of energy and increase of life result if no unnecessary measurement procedures and thus flashes are initiated by the triggering.

It can also be seen from FIG. 2 that, in the previously described manner, the holders for the insert elements, i.e. here the holding pins 42, are present in the region of the cuvette. Possible measurement deviations in the production of the insert elements or due to thermal expansion act, due to this measure, to a comparatively small extent on the distance of the element holders 42, 43 to the cuvette windows 30.

As already mentioned, the analysis elements preferably contain the reagents in a dry form already prepacked by the manufactrer because an especially simple operating of the apparatus is thereby possible, with a simultaneously high degree of flexibility. However, for special reactions, it can also be desirable to use liquid reagents, these preferably being first introduced into the apparatus in the analysis channel. FIG. 5 shows an appropriate analysis element 97 in radial cross-section through the middle of its analysis channel. It can be seen that the fluid channel 86 here forms an appropriate hollow chamber for the reception of a reagent which is limited by the barriers 100 and 101. The cover 102 of the liquid analysis element 97 contains a filling opening 98 for the reagent. The sample chamber 29, fluid channel 86, measuring chamber 84 and holding pin 42 are formed on the lower part 104 of the liquid analysis element 97, which is welded to the covering part 102.

For the operation of the liquid analysis element, an appropriate reagent is introduced through the opening 98 manually or with the help of a measuring device not shown in FIG. 1 and arranged on an appropriate circumference of the centrifugal analyzer. The subsequent analysis procedure takes place analogously to that in the known centrifugal analyzers, the advantage of the device according to the present invention being that, an insert elements in a rotor unit, there can be used those filled with various reagents and possibly differently shaped liquid analysis elements 97.

FIG. 6 shows a special embodiment of an analysis channel of an analysis element 16, 17, 18, 19, 20 or 21. There is an illustrated a cross-section roughly in the middle of the height of the fleece paper containing reagents according to FIG. 2, the cross-section running parallel to the rotor surface. There can be seen the sample chamber 29 and the fluid channel 86, as well as the fleece papers 88, 90 and 92 containing the reagents. The particular feature of the illustrated embodiment is that, radially feature towards the measurement chamber 84, two antechambers 106 are connected which serve for a supplementary mixing of the reagents dissolved out of the fleece papers 88, 90 and 92 with the sample solution.

In order to achieve this additional mixing action, the centrigual analyzer is, in one mixing run, accelerated and braked several times before the measurement, the reaction mixture thereby alternatingly penetrating at least partly into the antechambers 106 and then, when the acceleration in the peripheral direction (tangential acceleration) stops, again flowing back into the measuring chamber 84. A very good mixing up is achieved by means of this procedure. A mixing devices based on the same principle can also have a construction other than that here described, all that is necessary being that the antechambers 106 lie radially inwardly from the measuring chamber 84 and, via appropriate small barriers 108, are in connection therewith, the barriers have a height such that they can be at least partly overcome by the fluid in the case of accelerating or braking the rotor and, on the other hand, do not hinder the flowback of the fluid when there is no tangential acceleration.

In a preferred embodiment of the present invention, the walls 107 of the antechambers 106 are provided with a curvature which, in the illustrated cross-section, corresponds to an arc about a point which, on the connecting line between the measuring chamber 84 and the center of the analysis rotor, lies between these two points. This is indicated in FIG. 6 by dotted lines, the middle point of the curvature being indicated by K and the rotor center by Z.

FIGS. 7a and 7b show other devices which can be used for the additional mixing up of the reaction mixture. These are static mixing devices which can be arranged in the analysis elements in the fluid channel before the measuring chamber 84. The illustration is a cross-section in the plane as in FIGS. 2 and 5. The direction of flow of the reaction mixture is indicated by arrows. The mixing action is, in the case of FIG. 7a, achieved by baffles 110 which divide up the flow of fluid and again bring it together in order thereby to achieve a mixing action. These baffles can be case in one piece on the appropriate constructional parts of the analysis element. Another embodiment is illustrated in FIG. 7b, in which case a mesh structure 112 is introduced into the analysis element and fixed at an appropriate part in the fluid channel 86 and serves to divide up the reagent mixture current, again to bring it together and thus to mix it up.

In the following, there is explained the method of operating the device according to the present invention, the intermediate steps already previously explained in detail here being only briefly mentioned.

For programming the whole device, it is preferable to use a requirement card which can be completed by the investigating physician. A coding for the sample is contained therein in a mechanically readable form, with which is associated the name of the patient. This information is referred to as the sample identification. By means of appropriate mechanically readable marking, the so-called requirement profile is determined, i.e. the physician stipulates which components of the sample are to be analytically determined. The information is, in the following, called the analysis identification.

With the help of the previously described sample taking and preparing element, usable as a syringe, a blood sample is taken from the patient. The sample identification is, as coding 26, simultaneously applied to the insert element 22. This can take place, for example, by transferring an appropriate adhesive label present on the requirement card with a bar coding on to the appropriate surface of the sample obtaining and preparing element 22.

In the clinical laboratory with the device according to the present invention, the requirement cards of several patients are successively introduced into an appropriate reading device of the apparatus. In this way, the device obtains not only the sample identification but also the analysis identification. From these data, a calculator incorporated into the device determines the necessary loading of the rotor with the insert elements for the analyses to be carried out. Corresponding directions for the rotor loading are indicated on a picture screen device or by print out. The loading can also take place fully automatically. The loading of the rotors is carried out according to these instructions. This takes place, in the case of the previously described embodiment of the apparatus, in that, according to the directions, sample obtaining and preparing element 22 and analysis elements 16 to 21 are placed on the rotor base 12. After the rotor base 12 is loaded, the central closure 44 is closed. The loading of the rotor takes place in a manner which depends entirely upon the individual case. If, for example, only one analysis is needed, then, in addition to the sample obtaining and preparing element 22, merely a single analysis element 16 is set in place. The next sample can thereafter be placed on. In other cases, a particular, frequently repeating profile is required, i.e. a series of analyses important for a particular disease picture. For other purposes, corresponding multiple analysis elements 18, 20, 21 can be provided which, in their individual analysis channels, contain various reagents and in which the analysis channels can possibly also be constructed with different shapes. Such profile analysis elements make possible a particularly economic determination of frequently recurring profiles. If, in other cases, the same analysis is necessary for a number of samples, other multiple analysis elements can again be used which, in several analysis channels, contain reagents for the same determination. In this case, the appropriate sample obtaining and preparing elements filled with the samples are successively loaded onto the rotor base 12 and subsequently on the appropriate multiple analysis element. Finally, compendious and special analysis profiles can be fulfilled in a combination of single and multiple analysis element. It can be seen that, by means of the device according to the present invention, a great flexibility is possible. Handling is particularly simple because, especially in the case of the use of prepacked dry reagents, complicated manual steps are no longer necessary.

If a large sample throughout is required, it can be desirable to load the rotor unit with the insert elements away from the centrifugal analyzer. For this purpose, it is desirable to provide intermediate discs which are incorporated between the rotor base and the insert elements in the apparatus and thereby to load the insert elements away from the apparatus in an appropriate manner. The unit comprising the intermediate disc and the insert elements which, in this case, forms the rotor head, is then, in its totality, placed in the centrifugal analyzer. The intermediate discs permit several rotor heads to be loaded with inert elements and thus to prepare them for the measurement while the centrifugal analyzer is, for example, being used to carry out other analyses.

After the rotor head, equipped with the insert elements, has been placed in the apparatus and connected to the rotor base, therer follows the sample obtaining run of the rotor in which, in the sample obtaining and preparing elements, the sample, i.e. serum or plasma, can be obtained in the above described manner by centrifuging.

Thereafter follows the sample preparation which includes, in particular, the appropriate diluting, the stepwise functioning of the rotor drive according to the present invention thereby being used. The rotor is brought into a position in which the dilutor 34 stands precisely above the take-off opening of a sample obtaining and preparing element 22. Thereafter, the diluter 34 moves down vertically, penetrates the closure stopper 62, removes the sample by suction and again moves upwardly in order to introduce various diluted samples into the dilution chambers 72, 74 and 76 in the manner known for diluters. By means of the stepwise drive of the rotor, it is thereby, in each case, brought into the correct position under the diluter 34. The precise positioning of the rotor is simplified by the codings 24 provided on the rotor base, which can be read off by a reading device present on the apparatus and, in this manner, makes possible a precise control of the rotor.

The pre-diluting in the dilution chambers 72, 74 and 76 (see FIGS. 3 and 4) has the advantage that a comparatively large amount of sample can be diluted relatively exactly. The amount of sample transferred to the inlet openings 28 of the analysis elements is, on the other hand, very small. The dispenser 36 is provided for sucking out an amount of diluted sample sufficient for all the analyses to be carried out on a particular dilution of a particular sample and for dispensing it to the appropriate inlet openings of the sample chambers. Of course, the functions of the dilutor 34 and of the dispenser 36 can be fulfilled by a single unit but the use of two separate units is advantageous because a quicker loading of the analysis elements is thus obtained.

During the sample diluting and dispensing, the rotor moves stepwise back and forth, corresponding to the coding 24, under the control of the central unit of the centrifugal analyzer. The dosing units 34 and 36 thereby only have to perform vertical movements. Due to the thereby resulting mechanical simplicity of the drive making this movement possible, an economic construction and a great dependability of the apparatus is achieved.

Before the following mixture and measuring, any liquid analysis elements 97 present are provided with reagents.

After completion of the sample dilution and dispensing, there follows the mixing and measuring in which the centrifugal analyzer is brought to the speed of rotation necessary for the mixing and subsequent measuring. During this running, the codings 26 on the insert elements 16, 18, 20, 21 and 22 are read by the apparatus and compared with the fed-in sample identification and analysis identification. Should a discrepancy be observed, error indications are immediately given. In this way, an erroneous analysis due to false loading of the rotor with the insert elements is excluded with certainty. This control can, of course, also take place after loading or during the course of obtaining the sample.

For the varoius rotor runnings, in general different speeds of rotation are necessary. Of course, the necessary speeds of rotation depend upon the diameter of the rotor used. The highest speeds of rotation are, in normal cases, needed for centrifuging for obtaining serum or plasma samples. They are of the order of several thousand rotations per minute in the case of an effective rotor diameter of about 25 cm.

The speed of rotation during the mixing and measuring of the apparatus according to the present invention must be adjusted to the particular analysis insert elements employed. In the case of the use of liquid analysis elements, the experience gained from the use of conventional centrifugal analyzers can be used. Insofar as, according to an especially preferred embodiment of the present invention, use is made of the insert elements according to our above-mentioned Federal Republic of Germany Patent Specification No. 30 44 385, the speeds of rotation in the mixing and measuring runs of the apparatus are also to be chosen according to the instructions given in this German Patent Specification. In one example of this German Patent Specification, use is made of a comparatively small rotor of 33 mm. diameter in which the measurement circle diameter is 28 mm. The analysis channel is constructed according to the embodiment illustrated in FIG. 6, the fluid channel 86 thereby having a breadth of 1 mm. and a height of 6 mm. The fluid channel 86 contains fleece papers provided with dry reagents, the radial distance of which from the center of the rotor is from about 4 to 10 mm. Further details regarding the chemical composition of the dry reagents and further constructional details are given in our above-mentioned German Patent Specification. The course of measurement consists, in the case of the described measurements, for example of the determination of glucose described in our above-mentioned German Patent Specification, of the following steps:

1. Centrifuging at 2880 r.p.m. for 1 to 25 seconds. The diluted sample thereby penetrates into the first fleece paper and dissolves out the reagent.

2. Centrifuging at 12000 r.p.m. for 5 seconds. The solution is driven out of the fleece into the cuvette, only a minimal amount of solution remaining behind on the fleece.

3. A one second acceleration to 1200 r.p.m. and stopping of the rotor for a further second. This procedure is repeated 6 to 20 times, whereby, due to the tangential acceleration, the solution is driven into the antechambers 106 and a mixing effect is thereby achieved.

4. 4 seconds centrifuging at 12000 r.p.m. for sedimenting impurities and for driving out air bubbles.

5. Measuring at 2880 r.p.m.

If rotors of a different diameter are used or the insert elements with the analysis reagents have a different radial distance from the center of the rotor, corresponding speeds of rotation are to be used which lead to the same values for the centrifugal acceleration. Depending upon the dimensions and the analytical process used, however, an empirical determination of the most appropriate speeds of rotation is also necessary.

Since all insert elements which, in the case of a particular rotor running, are connected with the rotor are subjected to the same speed of rotation program, the analytical determinations simultaneously used must be so coordinated with one another that they can be carried out with the same speed of rotation program. As mentioned above, it is thereby possible also to make use of the fact that the centrifugal acceleration increases from the center to the periphery of the rotor. The radial arrangement, for example, of the fleece papers or other reagent carriers within the insert elements and/or the radial positioning of the insert element itself are thus, for example, determining for the centrifugal forces to which the dilute sample fluid or the reagent solution are subject in such a reagent carrier.

Further measures for the adaptation to the various analytical determinations to the given conditions are described in our above-mentioned German Patent Specification. By appropriate coordination of the various measures mentioned, it is possible to provide insert elements for a series of analytical determinations which can be measured with the same mixing and measuring run of the centrifugal analyzer.

What is claimed is:

1. A rotor unit for a centrifugal analyzer for analytically determining components of a sample, comprising:
a rotatably driven circular rotor base; and
a rotor head comprising a plurality of disposable insert elements and means for releasably mounting each insert element on the rotor base interchangeably at any one of a plurality of different selectable angular positions to positionally fix each insert element in place during rotation of the base and to enable the removal of each insert element after use,
wherein the plurality of insert elements include at least one rigid sample analysis insert element for determining at least one sample component and having at least one first means forming a sample chamber for the reception of a liquid sample,
at least one second means for forming a measuring chamber radially outwardly from the associated sample chamber when the sample analysis element is mounted on the base for the measurement of characteristic parameters during the rotation of a rotor head for the detection of components of a sample,
at least one third means comprising means defining a plurality of interconnected hollow space and forming a liquid channel connecting the sample chamber with the measuring chamber and configured for an analysis to be carried out, and
an analysis reagent in storage stable dry form positioned in the liquid chamber radially between the sample chamber and the measurement chamber for being mounted and removed with the analysis insert element and at least partly dissolvable by a sample to effect combination and mixing with a sample in response to the effect of centrifugal force before arriving at the measurement chamber.

2. The rotor unit according to claim 1, wherein the at least one rigid sample analysis insert element includes multiple sample analysis insert elements, each of said multiple sample analysis insert elements having a plurality of first, second and third means for the analytical determination of at least one component of at least one sample.

3. The rotor unit according to claim 1, wherein the rotor head further includes an intermediate disc and wherein the means for mounting the insert elements to the rotor base are formed on said intermediate disc.

4. The rotor unit according to claim 1, wherein the rotor base has machine readable coding thereon for effecting the reproducible and exact adjustment of particular rotor positions.

5. The rotor unit according to claim 1, wherein each of the insert elements, in plan view on the rotor base, is substantially sector-shaped.

6. The rotor unit according to claim 1, wherein the insert elements bear codings identifying at least one of a sample and components of a sample to be determined.

7. The rotor unit according to claim 1, wherein said at least one analysis insert element has triggering marks theron for starting a measurement procedure.

8. The rotor unit according to claim 1, wherein the at least one sample chamber, at least one liquid channel and at least one measuring chamber have a height along the axis of rotation of the rotor when, mounted and a width along radius of the rotor when mounted, the height and width being substantially greater than the depth, wherein their height and width comprise their major dimensions which are disposed in one plane and the means mounting each insert element disposes said one plane in a vertical orientation.

9. A rotor unit for a centrifugal analyzer for analytically determining components of a sample, comprising:
a rotatably driven circular rotor base, and a rotor head comprising a plurality of disposable insert elements and means for releasably mounting each insert element on the rotor base interchangeably at any one of a plurality of different selectable angular positions to positionally fix each insert element in place during rotation of the base and to enable the removal of each insert element after use,
wherein the plurality of insert elements include at least one rigid sample analysis insert element for determining at least one sample component and having at least one first means forming a sample chamber for the reception of a liquid sample,
at least one second means forming a measuring chamber radially outwardly from the associated sample chamber when the sample analysis element is mouted on the base for the measurement of characteristic parameters during the rotation of the rotor head for the detection of components of a sample, wherein the second means forming the measuring chamber is disposed in a first annular region at the periphery of the rotor head when the insert is mounted on the rotor base and includes means forming an optical window in the first annular region for optical measurement,
at least one third means forming a liquid channel connecting the sample chamber with the measuring chamber and configured for an analysis to be carried out, and
an analysis reagent in storage stable dry form positioned in the liquid channel radially between the sample chamber and the measurement chamber for being mounted and removed with the analysis insert element and at least partly dissolvable by a sample to effect combination and mixing with a sample in response to the effect of centrifugal force before arriving at the measurement chamber, and
wherein the means for releasably mounting each insert element on the rotor base comprises cooperating form-locking holding means on the rotor base in close proximity to the first annular region and on each at least one rigid sample analysis insert element in close proximity to the optical window, whereby the entire form-locking holding means when cooperating is disposed in close proximity to the optical window to maintain the position of the optical window to high precision for a normally low tolerance disposable insert element.

* * * * *